US00PP11999P2

(12) United States Plant Patent
Schmülling

(10) Patent No.: US PP11,999 P2
(45) Date of Patent: Jul. 17, 2001

(54) ASTERISCUS PLANT NAMED 'COMPACT GOLD COIN'

(75) Inventor: Markus Schmülling, Billerbeck (DE)

(73) Assignee: Outenique Protea Nursery, Emerald (AU)

( * ) Notice: Subject to any disclaimer, the term of this patent is extended or adjusted under 35 U.S.C. 154(b) by 0 days.

(21) Appl. No.: 09/369,466

(22) Filed: Aug. 6, 1999

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Asteriscus plant named 'Compact Gold Coin', characterized by its low spreading, mounding and compact plant habit; dark green foliage; numerous daisy-type inflorescences with widely-spaced ray florets; attractive bright lemon yellow ray florets; and excellent garden performance with good tolerance to high temperatures.

2 Drawing Sheets

BACKGROUND OF THE INVENTION

The present invention relates to a new and distinct cultivar of Asteriscus plant, botanically known as *Asteriscus maritimus* and referred to by the cultivar name Compact Gold Coin.

The new cultivar is a product of a planned breeding program conducted by the Inventor in Billerbeck, Germany. The objective of the breeding program is to develop new compact Asteriscus cultivars.

The new cultivar originated from a self-pollination made by the Inventor in 1993, of the *Asteriscus maritimus* cultivar Gold Coin, not patented.

The cultivar Compact Gold Coin was discovered and selected by the Inventor as a flowering plant within the progeny of the stated cross in a controlled environment in Billerbeck, Germany, in 1993. The selection of this new Asteriscus plant was based on its more compact and less upright plant habit compared to the parent cultivar, Gold Coin. In addition, ray florets of the new Asteriscus are more widely spaced than ray florets of the cultivar Gold Coin and are more tolerant to high temperatures.

Asexual reproduction of the new cultivar by terminal cuttings taken in a controlled environment in Billerbeck, Germany, and Bonsall, Calif., has shown that the unique features of this new Asteriscus are stable and reproduced true to type in successive generations.

SUMMARY OF THE INVENTION

The cultivar Compact Gold Coin has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Compact Gold Coin'. These characteristics in combination distinguish 'Compact Gold Coin' as a new and distinct cultivar:

1. Low spreading, mounding and compact plant habit.
2. Dark green foliage.
3. Numerous daisy-type inflorescences with widely-spaced ray florets.

4. Attractive bright lemon yellow ray florets.
5. Excellent garden performance, tolerant to high temperatures.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a top perspective view of a typical flowering plant of 'Compact Gold Coin'.

The photograph at the top of the second sheet is a close-up view of a typical plant of 'Compact Gold Coin'.

The photograph at the bottom of the second sheet is a close-up view of developing inflorescences and leaves of a typical plant of 'Compact Gold Coin'. Foliage and floret colors in the photographs may appear different from the actual colors due to light reflectance.

DETAILED BOTANICAL DESCRIPTION

The following observations, measurements and values describe plants of the new cultivar grown with three plants in a 25.5-cm container in Bonsall, Calif., under outdoor, full-sun conditions with day temperatures ranging from 18 to 35° C. and night temperatures ranging from 13 to 18° C.

Color references are made to The Royal Horticultural Society Colour Chart except where general terms of ordinary dictionary significance are used.

Botanical classification: *Asteriscus maritimus* cultivar Compact Gold Coin.

Parentage: Self-pollination of *Asteriscus maritimus* cultivar Gold Coin, not patented.

Propagation:

*Type.*—Terminal tip cuttings.

*Time to rooting.*—About 14 days with soil temperatures of 22° C.

*Root description.*—Fine.

Plant description:

*Appearance.*—Perennial herbaceous daisy-type garden Asteriscus. Low, compact, spreading and mounding growth habit. Freely branching with lateral branches potentially developing at every node.

*Crop time.*—From planting rooted cuttings, about 8 to 12 weeks are required to produce a finished, flowering plant.

*Vigor.*—Low to moderately vigorous.

*Plant height.*—About 10 cm.

*Plant spread.*—About 16 to 20 cm.

*Lateral branch description.*—Length: About 8 to 10 cm. Diameter: About 4 mm. Internode length: About 1 to 1.5 cm. Texture: Viscous; fuzzy. Color: 145B to 145C.

*Foliage description.*—Leaves alternate, single. Quantity: Numerous, about 16 per lateral branch. Length, fully expanded leaves: About 7.75 cm. Width, fully expanded leaves: About 1.85 cm. Shape: Oblanceolate. Apex: Obtuse. Base: Attenuate. Margin: Entire. Aspect: Mostly flat. Texture: Coarse; granular; slightly pubescent on both surfaces. Color: Young foliage, upper surface: 137B. Young foliage, lower surface: 137D. Fully expanded foliage, upper surface: 137A. Fully expanded foliage, lower surface: 137C. Attenuated leaf base: 144B to 144C. Venation, upper surface: 137A. Venation, lower surface: 137D.

Inflorescence description:

*Appearance.*—Daisy-type composite inflorescence form; actinomorphic. Single inflorescences displayed above foliage, about three inflorescences per lateral branch, upright on peduncles arising from leaf axils. Disc and ray florets arranged acropetally on a capitulum. Numerous inflorescences; typically about 32 opened and unopened inflorescences per plant. Inflorescences last about two weeks. Inflorescences persistent.

*Flowering response.*—Plants flower continuously from April to October in the Northern Hemisphere.

*Fragrance.*—Not detected.

*Inflorescence size.*—Diameter: About 3.6 cm. Depth (height): About 1.3 cm. Diameter of disc: About 1.7 cm.

*Inflorescence buds.*—Length: About 1 cm. Width: About 8 mm. Shape: Ovoid. Color: 1A.

*Ray florets.*—Length: About 1.7 cm. Width: About 4 mm. Shape: Ligulate. Apex: Tri-dentate. Base: Attenuate. Margin: Entire. Aspect: Flat; held upright, about 135° to peduncle; widely spaced. Texture: Smooth, satiny. Number per inflorescence: About 28 in a single whorl. Color: When opening, upper surface: 14B. When opening, lower surface 4B. Fully opened, upper surface: 14A. Fully opened, lower surface: 8A.

*Disc florets.*—Shape: Tubular. Number per inflorescence: Numerous, about 300. Length: About 6 mm. Width: About 2 mm. Color: Immature: 1C. Mature: 9B.

*Phyllaries.*—Shape: Ligulate. Apex: Rounded. Margin: Entire. Quantity: About 14 per inflorescence in a single whorl. Texture: Pubescent. Color: Upper surface: 146A. Lower surface: 147B.

*Peduncle.*—Length: About 1 cm. Aspect: Moderately strong, inflorescences held above and beyond foliage. Texture: Coarse; granular; pubescent. Color: 145B.

*Reproductive organs.*—Androecium: Present on disc florets only. Stamens: Five. Anther shape: Oblong. Anther size: About 1.5 mm. Anther color: 14A. Pollen amount: Moderate. Pollen color: 14A. Gynoecium: Present on ray and disc florets. Pistils: One. Pistil length: About 4 mm. Stigma shape: Bipartite. Stigma color: 9A. Style length: About 3 mm. Style color: 9D. Ovary color: 1D.

*Seed.*—Seed development has not been observed.

Disease resistance: Resistance to pathogens common to Asteriscus has not been observed on plants of the new Asteriscus.

Heat tolerance: Plants of the new Asteriscus have demonstrated good tolerance to high temperatures.

It is claimed:

1. A new and distinct cultivar of Asteriscus plant named 'Compact Gold Coin', as illustrated and described.

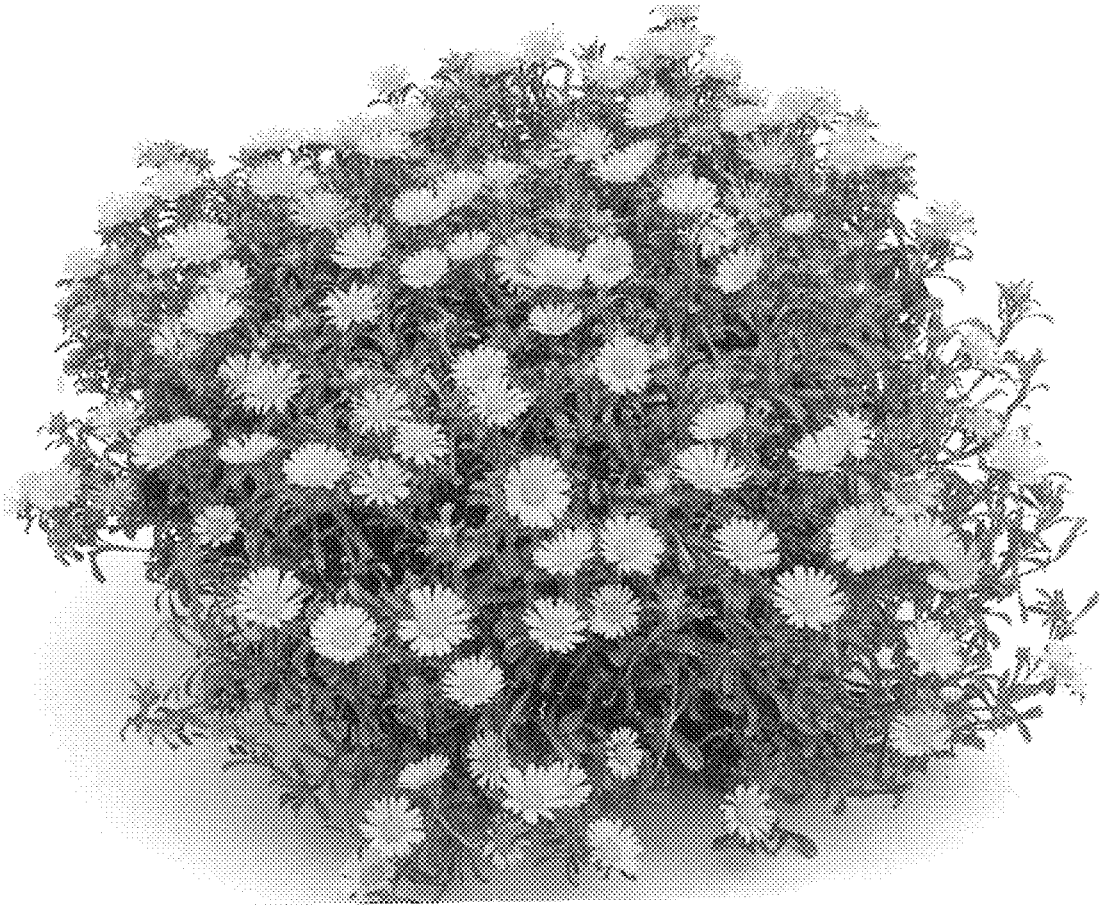

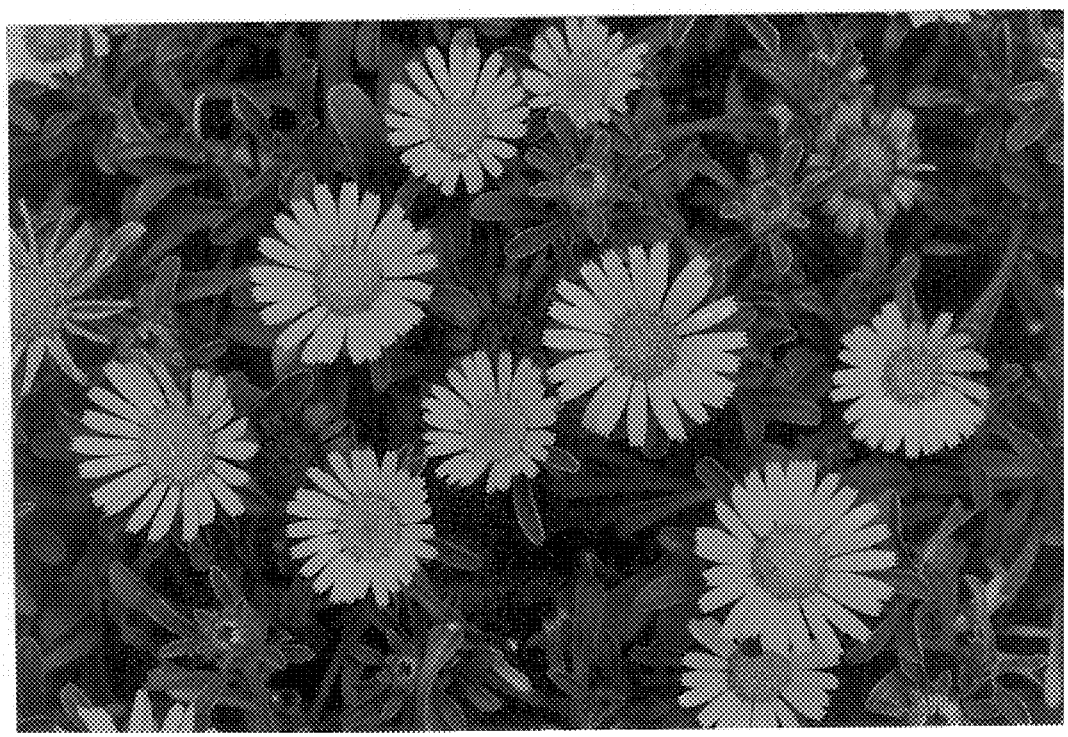
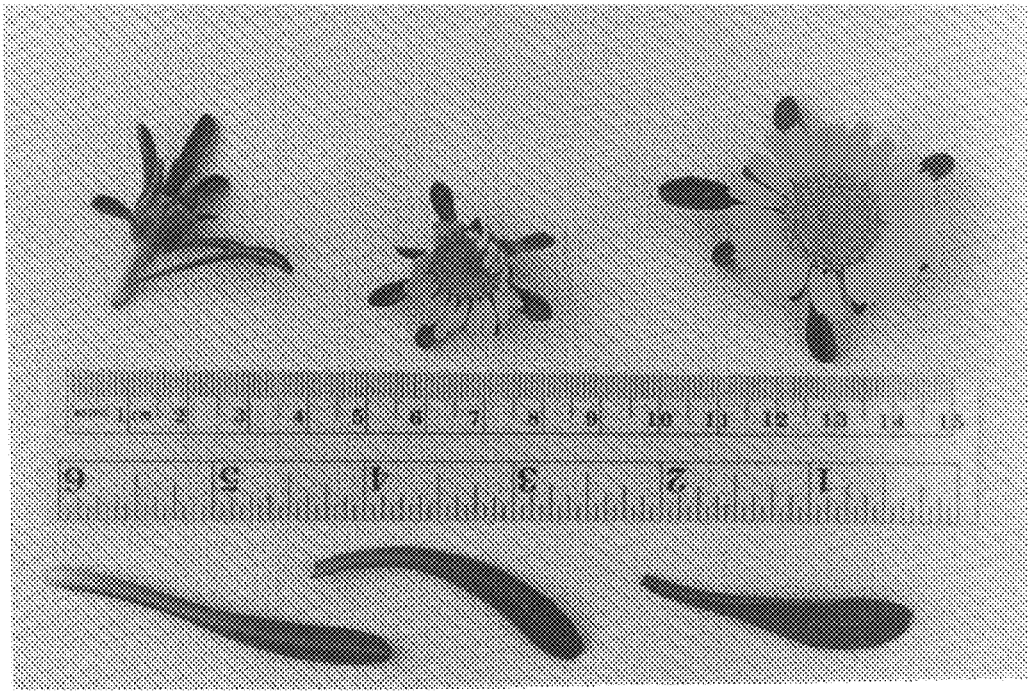

* * * * *